United States Patent [19]

Feldman et al.

[11] Patent Number: 5,009,634

[45] Date of Patent: Apr. 23, 1991

[54] METABOLIC CATHETER

[75] Inventors: Marc D. Feldman; Thomas C. Skalak, both of Charlottesville, Va.; Luiz Belardinelli, Gainesville, Fla.

[73] Assignee: The University of Virginia Alumni Patents Foundation, Charlottesville, Va.

[21] Appl. No.: 295,517

[22] Filed: Jan. 11, 1989

[51] Int. Cl.⁵ .............................................. A61M 1/00
[52] U.S. Cl. ........................................ 604/27; 604/35; 604/83
[58] Field of Search ...................... 604/27, 35, 36, 38, 604/43, 82, 83, 181, 182, 269, 28, 29, 44, 45, 52, 53, 56, 121, 241, 416, 902, 4–6; 128/207.14, 207.15, 632

[56] References Cited

U.S. PATENT DOCUMENTS

| | | | |
|---|---|---|---|
| 3,511,238 | 5/1970 | von Wrangell | 604/4 |
| 3,512,517 | 5/1970 | Kadish et al. | 604/27 |
| 3,610,226 | 10/1971 | Albisser | 604/27 |
| 3,916,892 | 11/1975 | Latham, Jr. | 604/83 |
| 3,965,896 | 6/1976 | Swank | 604/83 |
| 4,069,814 | 1/1978 | Clemens | 604/27 |
| 4,265,249 | 5/1981 | Schindler et al. | . |
| 4,316,466 | 2/1982 | Babb | 604/38 |
| 4,364,922 | 12/1982 | Berne et al. | . |
| 4,481,946 | 11/1984 | Altshuler et al. | 604/4 |
| 4,512,348 | 4/1985 | Uchigaki et al. | . |
| 4,601,697 | 7/1986 | Mammolenti et al. | . |
| 4,605,503 | 8/1986 | Bilstad et al. | 604/6 |

OTHER PUBLICATIONS

Ontyd and Schrader, "Measurement of Adenosine, Inosine, and Hypoxanthine in Human Plasma", Journal of Chromatography, 307:404–409 (Netherlands, 1981).

Primary Examiner—Randall L. Green
Assistant Examiner—K. Reichle
Attorney, Agent, or Firm—James Creighton Wray

[57] ABSTRACT

A metabolic catheter and method which allows the simultaneous removal of body fluids from organs and immediate addition of stop solution to the body fluid at the catheter tip to prevent degradation of the metabolite to be measured.

17 Claims, 1 Drawing Sheet

METABOLIC CATHETER

BACKGROUND OF THE INVENTION

1. Field of the Invention:

The present invention provides a metabolic catheter which is designed to achieve immediate mixing of two fluids during withdrawal of a first fluid. More specifically the present invention allows the simultaneous removal of body fluids from organs and the immediate addition of stop solution at the catheter tip to the body fluid to prevent degradation of the metabolite to be measured.

2. Prior Art:

U.S. Pat. No. 4,601,697 describes an indwelling double bore catheter which has a small mixing chamber at the distal end of the double bores. This allows for a better dilution and sampling of blood.

U.S. Pat. No. 4,364,922 describes a method of diagnosing atrioventricular conduction block caused by ischemia of the heart by measuring the time delay between the arterial and ventricular excitation before and after the administration of an adenosine antagonist.

U.S. Pat. No. 4,512,348 shows an invention which continuously and automatically monitors the concentration of specific blood constituents. The invention uses a double current catheter inserted into a vein.

U.S. Pat. No. 4,265,249 shows a semi-permeable filter catheter for taking samples from within fluid carrying members. A rinsing fluid is injected into this catheter.

Ontyd and Schrader in the article entitled "Measurement of Adenosine, Inosine and Hypoxanthine in Human Plasma" found in the *Journal of Chromatography*, 307, 404-409 (1981), which is printed in the Netherlands, disclose the use of an ice-cold "stopping" solution which consists of dipyridamole, NaCl, KCl, $NaHCO_3$, glucose, $CaCl_2$, $Na_2HPO_4$ and $NaH_2PO_4$ to prevent the degradation of adenosine. In addition this article describes a specially developed syringe system, where the "collecting" syringe was mechanically coupled with the syringe containing the "stopping" solution so that when the blood was drawn by pulling out the collecting syringe's plunger, the plunger of the "stopping" solution syringe was pushed in forcing the "stopping" solution to immediately mix with this aspirated blood in the collecting syringe's chamber. Therefore, this device achieved mixing only within the syringe device, whereas the current application achieves mixing at the sampling site, allowing measurement of metabolites from internal organs. This article also describes that due to the dimensions of the syringes a constant mixing ratio of 1:1 was achieved.

SUMMARY OF THE INVENTION

The present invention provides a means to allow the measuring of organ metabolites which have short half-lives of several seconds, such as those found in the heart or kidney. The use of the present invention allows the simultaneous removal of fluid from body organs and immediate addition to the fluid at the catheter tip of a stop solution to prevent degradation of the metabolites to be measured.

The metabolic catheter of the present invention has an infusion catheter aligned with a multipurpose angiographic catheter, which is used as a withdrawal catheter. Preferably the withdrawal catheter is 8 F with a soft, flexible, gently curving tip to minimize trauma when placing the catheter into position. Preferably, the distal end of the infusion catheter will be positioned 1 cm from the distal end of the withdrawal catheter. The combined metabolic catheter is placed in the coronary sinus, renal veins, or other blood vessels, to measure varieties of metabolites with very short half-lives of several seconds. A stop solution is injected into the tip of the withdrawal catheter via the infusion catheter, while blood from the coronary sinus or renal vein is being sampled through the withdrawal catheter. The stop solution, in the case of adenosine, will consist of dipyridamole, heparin and EDTA, which minimizes the degradation of adenosine by elements of the blood as blood moves through the withdrawal catheter In this manner, adenosine, which is a powerful marker of organ ischemia, can be measured, eliminating the problem of its short half-life.

The coupling of the injection of stop solution through the infusion catheter and withdrawal of blood through the withdrawal catheter uses two joined syringes Preferably, the plungers and barrels of the syringes are fastened together so that the infusing of a stop solution occurs with the withdrawal of the blood. These plungers can be fastened by machine screws, and the barrels can be firmly attached to adjustable braces. The syringe attached to the withdrawal catheter should have a barrel that is twice the cross-sectional area of the barrel of the syringe attached to the infusion catheter to insure 2-to-1 mixing of blood to stop solution. Preferably the syringe attached to the infusion catheter will be 3 cc in size, and the syringe attached to the withdrawal catheter will be 6 cc in size. There is a 2.01 cc of dead space between the withdrawal and infusion catheters and this dead space will be primed with stop solution prior to withdrawal of blood by the metabolic catheter. In the preferred invention the final ratio of blood to stop solution in the collection syringe drawn from a patient will be in the ratio of 1:4 for a total volume of 4 cc.

An additional stop solution which a patient cannot be exposed to can be added into the withdrawal syringe for the purpose of preventing production of the metabolite to be measured or preventing further degradation of the metabolite.

These and other and further objects and features of the invention are apparent in the disclosure which includes the above and ongoing specification with the claims and the drawings.

DETAILED DESCRIPTION OF THE DRAWINGS

Figure 1:
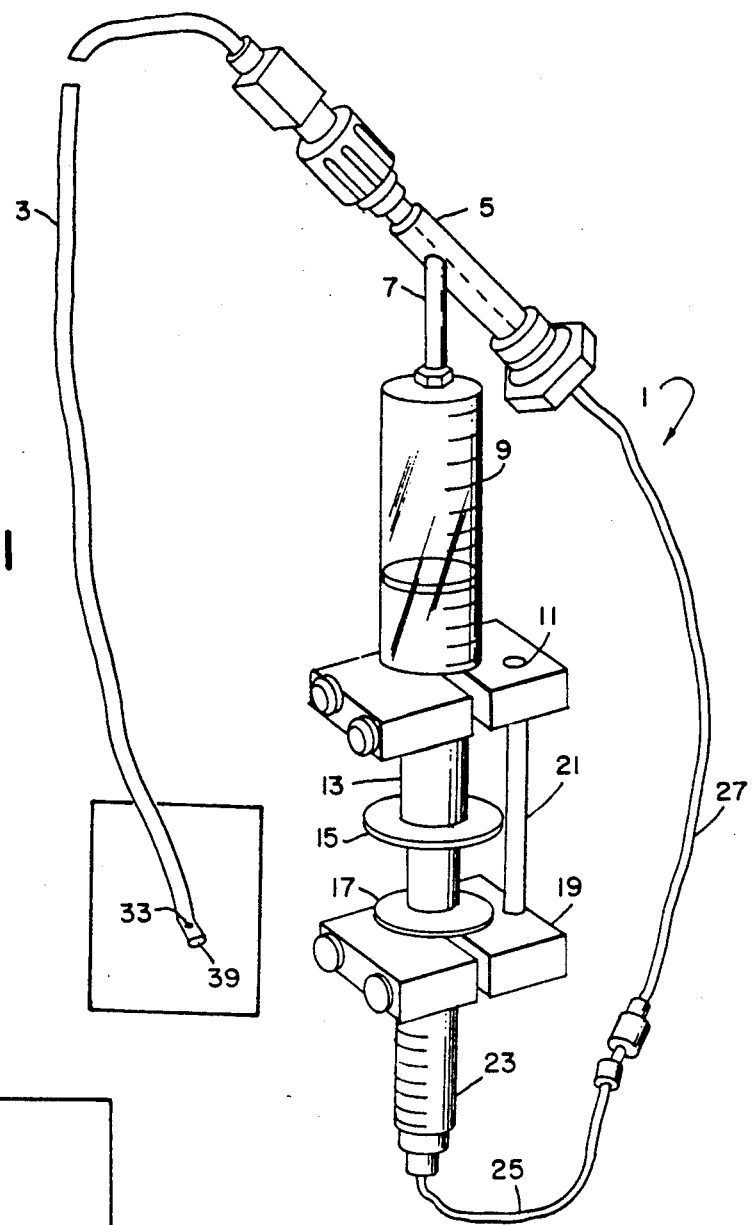
FIG. 1 shows a perspective view of the preferred embodiment of the invention.

FIG. 1 is a perspective view of the preferred embodiment of the present invention. The metabolic catheter generally referred to as 1 consists of a withdrawal catheter 3 in which an infusion catheter 27 is inserted. This withdrawal catheter 3 is a multipurpose angiographic catheter The withdrawal catheter 3 has an opening 39 at the distal end and two smaller openings 33 and 37 on opposite sides near the distal end. The withdrawal catheter 3 and the infusion catheter 27 are connected to a Y adaptor 5 with O ring (not shown). Angled stem 7 of Y adaptor 5 is connected to the open end of collecting syringe 9. Collecting syringe 9 is held in place by adjustable bracket 11. The plunger 13 of collecting syringe 9 is fastened by a pair of machine screws 15 to plunger 17 of infusion syringe 23. Infusion syringe 23 is held in place by wall bracket 19. Wall brackets 11, 19 are positioned apart by support 21. A plastic tube 25 is connected to the opening of infusion syringe 23. The plastic tube 25 is then connected to the infusion catheter 27 which is in turn inserted through the Y adaptor 5 and the withdrawal catheter 3.

As plunger 13 of collection syringe 9 is pulled out, blood flows into the withdrawal catheter 3 and into the collection syringe 9. At the same time as plunger 13 is pulled out, plunger 17 of infusion syringe 23 is pushed into infusion syringe 23 and infuses the stop solution through tube 25 and the infusion catheter 27 so that mixing between the stop solution and the blood occurs at the distal end of the withdrawal catheter, as blood enters withdrawal catheter 3.

Figure 2:
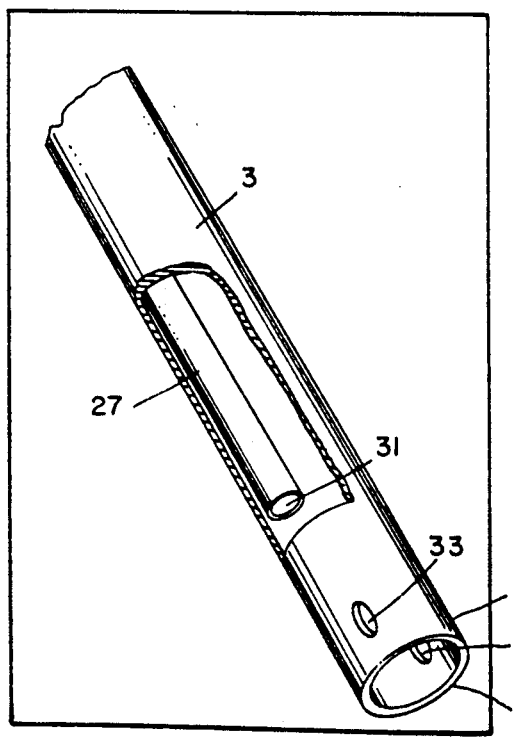
FIG. 2 shows an enlarged section of the distal end of the withdrawal catheter which includes a cutaway to expose the infusion catheter.

FIG. 2 is an enlarged area of the distal end of withdrawal catheter 3 which provides a cutaway area to expose the position of the tip of infusion catheter 27. Infusion catheter 27 is positioned 1 cm from the end of withdrawal catheter 3 and creates 2.01 cc of dead space between the withdrawal and infusion catheters. It is this dead space which will be primed with stop solution prior to withdrawal of blood by the metabolic catheter. Infusion catheter 27 has an opening 31 at its distal end. The withdrawal catheter has a tapered end 35 and has an opening 39 at its distal end and two smaller openings 33, 37 on the sides of the catheter near its distal end.

In validating the metabolic catheter, a precision-bore glass tube was used to simulate the withdrawal catheter, allowing direct microscopic visualization to document mixing of blood and stop solution at the catheter tip. An infusion catheter was inserted into the glass tube, and the system was connected to coupled infusion-withdrawal pumps for control of the flow rate. Dextran solutions with viscosities equal to those of blood at 37° C. and stop solution at 25° C. were used. The dextran stop solution also contained 2% Cresyl Blue to provide contrast for flow visualization. Observations were made using an AO microscope and a 3.5 X Leitz long working distance objective, and photographed for analysis of the flow field. Measurements were made for a range of Reynolds numbers (Re) of 10 to 100, corresponding to the possible range of flow rate of 0.07 to 0.70 ml/sec during blood withdrawal through the metabolic catheter.

The results show that adequate mixing occurs at the tip of the metabolic catheter if the Re is maintained at a value greater than 52 or a flow rate of 0.32 ml/sec corresponding to withdrawal of a 4 cc sample in 12.5 seconds. At this Re, the stop solution is distributed uniformly across the lumen of the withdrawal catheter, and large vortices develop in the injection region, insuring that adenosine present at the tip of the metabolic catheter will be mixed with stop solution.

Experiments were performed to determine that the metabolic catheter prevents degradation of adenosine by blood elements. As adenosine in coronary sinus blood enters and travels in the metabolic catheter, it can be taken up by blood elements including erythrocytes, platelets, and lymphocytes. These blood elements contain adenosine deaminase and nucleotidase which can degrade adenosine to hypoxanthine and iosine. Two conditions were designed to determine if the metabolic catheter plus stop solution can prevent this degradation of adenosine. In the control condition, human blood drawn through the withdrawal catheter had $C_{14}$ adenosine added at the tip of the infusion catheter but no stop solution. In the experimental condition, human blood drawn through the withdrawal catheter had stop solution plus $C_{14}$ adenosine added at the tip of the infusion catheter. By comparing the results of these two conditions, the amount of $C_{14}$ adenosine taken up by blood elements and degraded during transit of blood through the metabolic catheter could be determined.

The preliminary data indicate that in the control condition (blood plus $C_{14}$ adenosine mixed at the tip of the catheter, no stop solution) $88 \pm 6\%$ of the $C_{14}$ is taken up into the cellular elements of blood (n=4), as opposed to the experimental condition (blood plus $C_{14}$ adenosine plus stop solution are all mixed at the tip of the catheter) where $28 \pm 6\%$ of $C_{14}$ adenosine is taken up into cellular elements of blood (n=4). Further analysis of the supernatant revealed that in the control condition, $12 \pm 4\%$ of the radioactivity is adenosine (other 88% is adenosine degradation products, n=4) as opposed to the experimental condition where $98 \pm 0.1\%$ of the radioactivity is adenosine (other 2% is adenosine degradation products, n=4). These results demonstrate that the metabolic catheter markedly reduces the uptake of adenosine by blood elements, and its subsequent degradation.

Preferably, the stop solution used with adenosine consists essentially of 0.2 mM of dipyridamole, 25 units/ml of heparin and 4.2 mM of EDTA.

Further, an additional stop solution can be added to prevent production of additional metabolites by blood elements or to prevent further degradation of the metabolites. However, this additional stop solution cannot come in contact with the patient and is therefore added to the withdrawal syringe before withdrawing the sample fluid. Preferably, when adenosine is being measured, this additional stop solution will consist essentially of 5 $\mu$M of erythro-9-2-hydroxy-3-nonyl adenine (EHNA) and $6.2 \times 10^{-5}$ M of alpha, beta-methyleneadenosine 5'-nucleotide (AOPCP).

In this way the patient's blood will mix at the tip of the metabolic catheter with the components in the first stop solution, travel through the catheter, and upon removal from the body and entry into the withdrawal syringe, mix with the components of the additional stop solution.

While the invention has been described with reference to specific embodiments, modifications and variations of the invention may be constructed without departing from the scope of the invention which is defined in the following claims.

We claim:

1. A metabolic catheter comprising:
   (a) a withdrawal catheter having proximal and distal ends;
   (b) an infusion catheter having proximal and distal ends, wherein the infusion catheter is inserted within the withdrawal catheter and positioned so that the distal end of the infusion catheter is near the distal end of the withdrawal catheter and provides a space between distal ends of the withdrawal and infusion catheters;
   (c) first and second syringes, wherein the first syringe is attached to the proximal end of the withdrawal catheter and the second syringe is attached to the proximal end of the infusion catheter, wherein plungers of the first and second syringes are fastened together end-to-end and are mounted; and (d) a first stop solution which is placed into the second syringe attached to the infusion catheter, wherein the metabolic catheter further comprises a second stop solution which is placed into the first syringe attached to the withdrawal catheter.

2. The apparatus of claim 1, wherein the infusion catheter is positioned about 1 cm from the end of the withdrawal catheter and provides a 2.01 cc of dead space between the distal ends of the withdrawal and infusion catheters.

3. The apparatus of claim 1, wherein the first syringe attached to the withdrawal catheter is twice the cross-sectional area of the second syringe attached to the infusion catheter.

4. The apparatus of claim 1, wherein the first syringe attached to the withdrawal catheter is about 6 cc and the second syringe attached to the infusion catheter is about 3 cc.

5. The apparatus of claim 1, comprising means for adding the second stop solution to the first syringe before withdrawing the sample fluid, wherein the sample fluid mixes with the second stop solution so that the second stop solution cannot come in contact with a patient.

6. The apparatus of claim 5, wherein the second stop solution comprises 5 $\mu M$ of erythro-9-2-hydroxy-3-nonyl adenine and $6.2 \times 10^{-5}$ M of alpha, beta-methyleneadenosine 5'-nucleotide.

7. The apparatus of claim 1, wherein the first syringe attached to the withdrawal catheter is about 6 cc and this syringe acts as a collection syringe.

8. The apparatus of claim 1, wherein the second syringe attached to the infusion catheter is about 3 cc and acts to infuse the stop solution through the infusion catheter.

9. The apparatus of claim 1, wherein the first stop solution comprises dipyridamole, heparin and EDTA.

10. The apparatus of claim 1, wherein the first stop solution comprises 0.2 mM of dipyridamole, 25 units/ml of heparin, and 4.2 mM of EDTA.

11. The apparatus of claim 1, wherein the withdrawal catheter is 8 F.

12. The apparatus of claim 1, wherein the syringes include means for mixing of blood to stop solution in a ratio of 2:1.

13. The apparatus of claim 1, wherein the syringes include means for attaining a final ratio of blood to stop solution in the collection syringe of 1:4 for a total volume of 4 cc.

14. The apparatus of claim 1, wherein the distal end of the withdrawal catheter includes means for placement within the coronary sinus.

15. The apparatus of claim 1, including means for mixing the blood and stop solution to provide an Re of at least 52, or a flow rate of at least 0.32 ml/sec., corresponding to withdrawal of a 4 cc sample in 12.5 seconds.

16. The apparatus of claim 1, further comprising:
(a) wherein the first stop solution comprises dipyridamole, heparin and EDTA; and
(b) means for immediately mixing the first stop solution with the blood in the space between the distal ends of the infusion and withdrawal catheters immediately upon the withdrawing of the blood into the withdrawal catheter, wherein the mixing of blood to stop solution is in a ratio of 2:1.

17. The apparatus of claim 1, wherein the distal end of the withdrawal catheter includes means for placement within the renal vein.

* * * * *